(12) United States Patent
Ueno

(10) Patent No.: US 8,337,891 B2
(45) Date of Patent: Dec. 25, 2012

(54) ENTERIC COATED COMPOSITION COMPRISING PROSTAGLANDIN ANALOGS AS CHLORIDE CHANNEL OPENER

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 1470 days.

(21) Appl. No.: 10/562,637

(22) PCT Filed: Jul. 5, 2004

(86) PCT No.: PCT/JP2004/009867
§ 371 (c)(1),
(2), (4) Date: Jun. 1, 2006

(87) PCT Pub. No.: WO2005/002588
PCT Pub. Date: Jan. 13, 2005

(65) Prior Publication Data
US 2006/0240106 A1     Oct. 26, 2006

Related U.S. Application Data

(60) Provisional application No. 60/484,304, filed on Jul. 3, 2003.

(51) Int. Cl.
*A61K 9/24* (2006.01)
*A61K 9/28* (2006.01)

(52) U.S. Cl. .................................. 424/472; 424/474

(58) Field of Classification Search .................. None
See application file for complete search history.

(56) References Cited

U.S. PATENT DOCUMENTS

| | | | | |
|---|---|---|---|---|
| 4,198,405 A * | 4/1980 | Enomoto et al. | | 514/530 |
| 4,364,951 A * | 12/1982 | Skuballa et al. | | 514/320 |
| 5,047,525 A * | 9/1991 | Raduechel et al. | | 536/103 |
| 5,073,569 A | 12/1991 | Ueno et al. | | |
| 5,166,174 A | 11/1992 | Ueno et al. | | |
| 5,212,324 A | 5/1993 | Ueno | | |
| 5,221,763 A | 6/1993 | Ueno et al. | | |
| 5,739,161 A | 4/1998 | Ueno | | |
| 6,197,329 B1 * | 3/2001 | Hermelin et al. | | 424/441 |
| 6,242,485 B1 | 6/2001 | Ueno | | |
| 6,583,174 B1 * | 6/2003 | Ueno et al. | | 514/456 |
| 2003/0119898 A1 * | 6/2003 | Ueno et al. | | 514/456 |
| 2003/0166632 A1 | 9/2003 | Ueno | | |
| 2004/0138308 A1 * | 7/2004 | Ueno et al. | | 514/573 |
| 2006/0063830 A1 * | 3/2006 | Ueno | | 514/469 |

FOREIGN PATENT DOCUMENTS

| | | | |
|---|---|---|---|
| EP | 0930296 A1 * | 9/1997 | |
| EP | 0979651 A1 * | 9/1998 | |
| EP | 0 979 651 A | 2/2000 | |
| JP | 59-155325 A | 9/1984 | |
| JP | 5-139964 A | 6/1993 | |
| JP | 2000-319166 A | 11/2000 | |
| WO | 98/02148 A2 | 1/1998 | |
| WO | WO 02/20007 A | 3/2002 | |
| WO | WO 03/030912 A | 4/2003 | |
| WO | WO 03030912 A1 * | 4/2003 | |
| WO | WO 2004/037268 A | 5/2004 | |
| WO | WO 2005002588 A1 * | 1/2005 | |

OTHER PUBLICATIONS

Sue Gotham; Crohn's disease, constipation and IBS; IDrugs Jul. 1, 2003; vol. 6, No. 7, p. 635-638.

* cited by examiner

*Primary Examiner* — Robert A Wax
*Assistant Examiner* — Olga V Tcherkasskaya
(74) *Attorney, Agent, or Firm* — Sughrue Mion, PLLC

(57) ABSTRACT

The present invention provides an enteric coated composition for oral administration of a chloride channel opener which can provide improved pharmaceutical activity with reduced adverse side effect such as nausea.

11 Claims, 1 Drawing Sheet

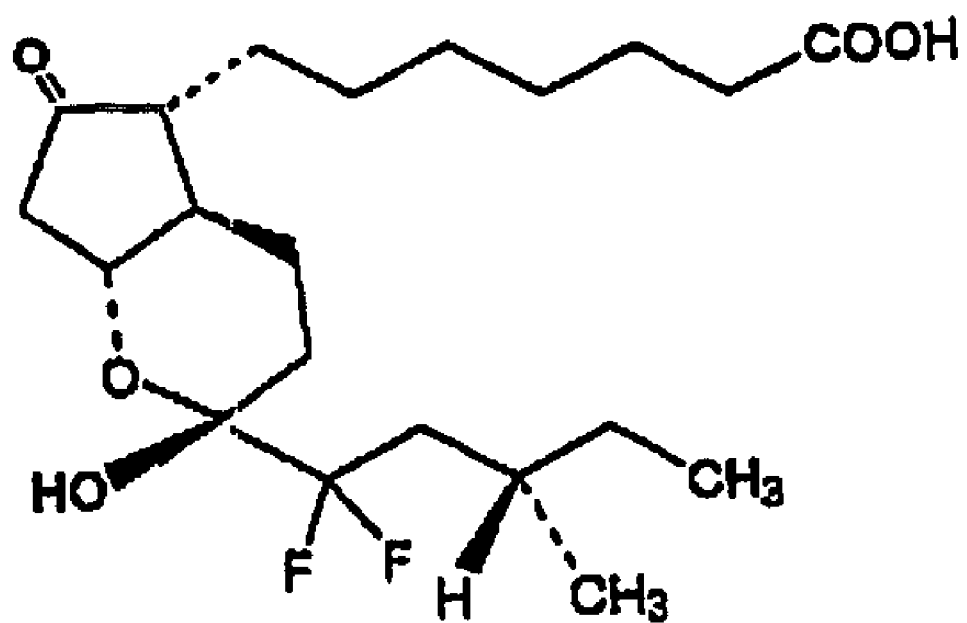

ENTERIC COATED COMPOSITION COMPRISING PROSTAGLANDIN ANALOGS AS CHLORIDE CHANNEL OPENER

This application claims benefit of U.S. Provisional Application No. 60/484,304 filed on Jul. 3, 2003, the entire disclosure of which is incorporated herein by reference.

TECHNICAL FIELD

The present invention relates to an enteric coated composition for oral administration comprising a chloride channel opener as an active ingredient thereof.

BACKGROUND ART

Prostaglandins (hereinafter, referred to as PG(s)) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

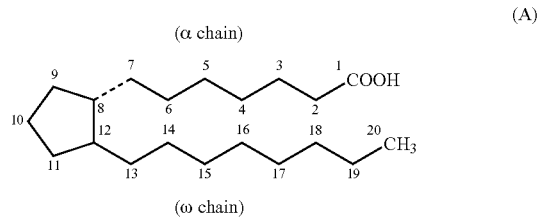

(A)

On the other hand, some of synthetic analogues of primary PGs have modified skeletons. The primary PGs are classified to PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:
Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9- and 11-position, into α type (the hydroxyl group is of an α-configuration) and β type (the hydroxyl group is of a β-configuration).

$PGE_1$ and $PGE_2$ and $PGE_3$ are known to have vasodilation, hypotension, gastric secretion decreasing, intestinal tract movement enhancement, uterine contraction, diuretic, bronchodilation and anti ulcer activities. $PGF_{1\alpha}$, $PGF_{2\alpha}$ and $PGF_{3\alpha}$ have been known to have hypertension, vasoconstriction, intestinal tract movement enhancement, uterine contraction, lutein body atrophy and bronchoconstriction activities.

The present inventor has already found that prostaglandin compounds open chloride channels, especially ClC channels, more especially ClC-2 channel (US patent publication No. 2003-0130352, this cited reference is herein incorporated by reference). Further, the present inventor has already found that chloride channel openers have wide range of pharmacological activities (US patent publication Nos. 2003-0130352 and 2003-0166632, these cited references are herein incorporated by reference).

The chloride channel opener for the treatment of constipation was reported to have an adverse event such as nausea (Annual Meeting of the Digestive Disease Week. 372, 2003 (Abstract)).

However, it is not known how to relieve the adverse event such as nausea of the chloride channel openers.

DISCLOSURE OF THE INVENTION

An object of the present invention is to provide a composition for oral administration of a chloride channel opener which can provide improved pharmaceutical effect to the living body with reduced adverse side effect such as nausea.

Namely, the present invention relates to an enteric coated composition for oral administration comprising a chloride channel opener as an active ingredient thereof and an enteric coating.

DETAILED DESCRIPTION OF THE INVENTION

The chloride channel opener used in the present invention is not particularly limited and may be any compound as far as it has a chloride channel opening activity. The chloride channel opening activity may be confirmed by measuring the increase of chloride-ion flows through a chloride channel in a cell membrane from inside to outside of the cell or in the opposite direction. For instance, it is possible to screen compounds for chloride channel opening activity by using a known assay strategy such as the patch clamp techniques. Preferred chloride channel opener is a ClC channel opener, especially a ClC-2 channel opener.

Examples of compounds having ClC-2 channel opening activity include cyclooxygenase inhibitor, nonsteroidal anti-inflammatory agent (e.g. ibuprofen and ebselen), protein kinase A, oleic acid, elaidic acid, arachidonic acid, cell growth factor (e.g., transforming growth factor-α ($TGF_\alpha$) and keratinocyte growth factor (KGF)), benzimidazole derivative and prostaglandin compound. Preferred compound used in the present invention is a prostaglandin compound.

The nomenclature of the PG compounds used herein is based on the numbering system of the prostanoic acid represented in the above formula (A).

The formula (A) represents a basic skeleton of a Prostaglandin compound having 20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-dehydroxy-PG compound.

As stated above, the nomenclature of the PG compounds is based on the prostanoic acid skeleton. However, in case the compound has a similar partial structure as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

Examples of the analogs (including substituted derivatives) or derivatives include a PG compound of which carboxy group at the end of α-chain is esterified; a compound of which α-chain is extended; physiologically acceptable salt thereof; a compound having a double bond at 2-3 position or a triple bond at position 5-6, a compound having substituent(s) at position 3, 5, 6, 16, 17, 18, 19 and/or 20; and a compound having lower alkyl or a hydroxy (lower)alkyl group at position 9 and/or 11 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substuents at position 5 include halogen atoms such as chlorine and fluorine. Preferred substituents at position 6 include an oxo group forming a carbonyl group. Stereochemistry of PGs having hydroxy, lower alkyl or hydroxy(lower)alkyl substituent at position 9 and/or 11 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

A preferred prostaglandin compound used in the present invention is represented by the formula (I):

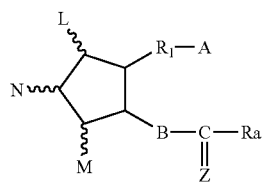

(I)

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —CH$_3$, or —CH$_2$OH, —COCH$_2$OH, —COOH or a functional derivative thereof;

B is —CH$_2$—CH$_2$—, —CH=CH— or —C≡C—;

Z is

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group or heterocyclic-oxy group.

A more preferred prostaglandin compound used in the present invention is represented by the formula (II):

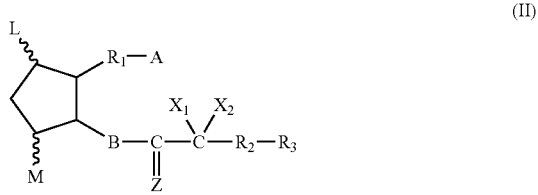

(II)

wherein L and M are hydrogen, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —CH$_3$, or —CH$_2$OH, —COCH$_2$OH, —COOH or a functional derivative thereof;

B is —CH$_2$—CH$_2$—, —CH=CH— or —C≡C—;

Z is

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$ and X$_2$ are hydrogen, lower alkyl, or halogen;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;

R$_2$ is a single bond or lower alkylene; and

R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group.

In the above formula, the term "unsaturated" in the definitions for $R_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy(lower) alkyl esters such as methoxymethyl ester and 1-methoxyethyl ester; and optionally substituted aryl esters' such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A means a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonylamide and tolylsulfonylamide.

Preferred examples of L and M include hydroxy and oxo, and especially, M is hydroxy and L is oxo which has a 5-membered ring structure of, so called, PGE type.

Preferred example of A is —COOH, its pharmaceutically acceptable salt, ester or amide thereof. Preferred example of $X_1$ and $X_2$ is fluorine, so called 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur. Examples of $R_1$ include, for example, the following groups:

—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$—CH=CH—,
—$CH_2$—C≡C—$CH_2$—$CH_2$—$CH_2$—,
—$CH_2$—$CH_2$—$CH_2$—$CH_2$—O—$CH_2$—,
—$CH_2$—CH=CH—$CH_2$—O—$CH_2$—,
—$CH_2$—C≡C—$CH_2$—O—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—,
—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—$CH_2$—CH($CH_3$)—$CH_2$—,
—$CH_2$—$CH_2$—$CH_2$—$CH_2$—CH($CH_3$)—$CH_2$—,
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—$CH_2$—, and
—$CH_2$—$CH_2$—$CH_2$—$CH_2$—$CH_2$—$CH_2$—CH($CH_3$)—$CH_2$—.

Preferred Ra is a hydrocarbon containing 1-10 carbon atoms, more preferably, 1-8 carbon atoms. Ra may have one or two side chains having one carbon atom.

The configuration of the ring and the α- and/or ω chains in the above formulae (I) and (II) may be the same as or different from that of the primary PGs. However, the present invention also includes a mixture of a compound having a primary type configuration and a compound of a non-primary type configuration.

In the present invention, PG compounds of formula (II) wherein B is —$CH_2$—$CH_2$—, M is hydroxy and Z is keto (=O) may be in the keto-acetal equilibrium by forming hemiacetal bonding between the hydroxy at position 11 and keto at position 15.

For example, it has been revealed that when both of $X_1$ and $X_2$ are halogen atoms, especially, fluorine atoms, the compound of formula (II) contains a tautomeric isomer, i.e. a bicyclic compound in addition to the monocyclic compound. If such tautomeric isomers are present, the proportion of them varies with structure of the rest of the molecule, the substituent on the molecule as well as the surrounding condition. Sometimes one isomer may predominantly be present in comparison with the other. However, it is appreciated that the compounds used in the present invention includes both isomers. That is, in the specification and claims, while the compounds used in the invention may be represented by a formula or name based on the keto-type regardless of the presence or absence of the isomers, it is to be noted that such structure or name does not intend to exclude the acetal type compound unless otherwise indicated. In other word, 15-keto-PG compound coevrs a bicyclic tautomer of the same unless otherwise indicated.

A typical example of the bicyclic tautomer of 15-keto-PG is represented by the formula (III):

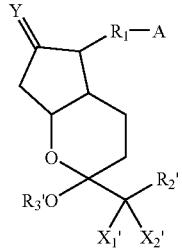

(III)

wherein, A is —$CH_3$, or —$CH_2OH$, —$COCH_2OH$, —COOH or a functional derivative thereof;
$X_1'$ and $X_2'$ are hydrogen, lower alkyl, or halogen;
Y is

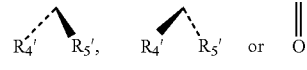

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time;
$R_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;
$R_2'$ is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group; and
$R_3'$ is hydrogen, lower alkyl, cyclo(lower)alkyl, aryl or heterocyclic group.

U.S. Pat. No. 6,414,016 (this cited reference is herein incorporated by reference) discloses that a prostaglandin compound having bicyclic structure is useful for relieving or preventing constipation and that the enteropooling effect of the same is enhanced as the ratio of the bicylic tautomer to monocyclic tautomer increases.

As shown in the test examples below, more than 5% of the bicyclic tautomer is converted into the corresponding monocyclic tautomer under the condition of pH 2. The data suggests that by protecting the bicyclic tautomer from the acidic condition, such as gastric juice, with an enteric coating, ring opening of the bicyclic compound under said condition is effectively prevented, and the ratio of the bicyclic tautomer is effectively kept. Accordingly in one embodiment of the present invention, an enteric coated composition comprising a bicyclic compound of formula (III) and an enteric coating is provided. The composition may further comprise a monocyclic tautomer of said bicyclic compound.

As is shown in U.S. Pat. No. 6,414,016, the composition comprising the bicyclic compound of formula (III) is effective not only for relieving or preventing constipation in a constipated patient, but also for cleansing a bowel of a patient.

For the treatment of constipation and/or cleansing bowel, the ratio of the bicyclic compound of formula (III) to the monocyclic tautomer of the compound is preferably at least 1:1, more preferably at least 20:1 or even greater to substantially all bi-cyclic compound.

U.S. Pat. No. 6,583,174, the content of the reference is herein enclosed by reference, discloses that the bicyclic compound of formula (III) is effectively stabilized by dissolving the same in a glyceride, preferably that of a fatty acid having 6-24, especially 6-20 carbon atoms. Accordingly, in one embodiment of the present invention, the composition may comprise the bicyclic compound of formula (III), glyceride and an enteric coating in which the bi-cyclic compound is present in a ratio of at least 1:1, especially, 20:1 with respect to its tautomeric monocyclic compound. Said composition may be formulated as capsule and outer surface of the capsule may be coated by the enteric coating, or enteric materials may be compounded into the capsule base. On the other hand, the compound of formula (III) may be provided as solid product comprising substantially no monocylic tautomer of the same and one embodiment of the present invention covers an composition comprising the compound of formula (III) and a enteric coating, wherein said composition comprises substantially no monocyclic tautomer of the compound.

Some of the compounds used in the present invention may be prepared by the method disclosed in U.S. Pat. Nos. 5,073, 569, 5,166,174, 5,221,763, 5,212,324, 5,739,161 and 6,242, 485 (these cited references are herein incorporated by reference).

The term "chloride channel opener", "ClC channel opener" or "ClC-2 channel opener" used herein includes a compound which activates, promotes or modulates the Cl⁻ current, Cl⁻ secretion or Cl⁻ transport by opening the chloride, ClC or ClC-2 channel.

The enteric coatings, which may be used in the present invention, may be any of the enteric coating conventionally used in the drugs. Examples of the enteric coatings may include carboxymethyl ethylcellulose, hydroxypropyl methylcellulose phthalate, cellulose acetate phthalate, cellulose acetate butylate, cellulose acetate trimellitate, hydroxypropyl methylcellulose acetate succinate, methacrylic acid copolymers such as methacrylate-methacylate methyl copolymer, methacylate and methacylrate-achylate ethyl copolymer, but not limited thereto. The enteric coating may be used solely or in combination with one or more other enteric coatings. Enteric coatings such as the one as described in WO2004/30658, the content of which is herewith incorporated by reference, is preferably used.

The enteric coating may optionally contain pharmaceutically acceptable plasticizers. Examples of plasticizers include triacetin, citric acid esters, phthalic acid esters, dibutyl sebacate, cetyl alcohol, polyethylene glycols and polysorbates, but not limited thereto. Further, the enteric coating may include additives such as dispersing agents, colorants, pigments, polymers, anti-adhesive agent, anti-bubbling agent, etc.

The method for formulating the enteric coated composition of the present invention may not be limited. It may be formulated according to any of conventional manners. For example, the powder and granule may be formulated by covering the enteric coating according to the conventional manner. Further, the capsule may be formulated by covering the enteric coating outside the conventional film such as gelatin film, filling the enteric coated powder or granule into the conventional capsule, or mixing the enteric materials into the capsule base. Further more, the tablet may be formulated by covering the enteric coating outside the conventional tablet, or compressing the enteric coated powder or glandule.

The present composition may be a controlled release enteric coated formulation. The examples of controlled releasing enteric coating are aminomethacrylate copolymer, acrylate ethylmethacrylate methyl copolymer, ethylcellulose, hydroxypropyl methylcellulose, hydroxypropylcellulose, carboxyvinyl polymer.

The dose may vary depending on the strain of the animal, age, body weight, symptom to be treated, desired therapeutic effect, administration route, term of treatment and the like. A satisfactory effect can be obtained by systemic administration 1-6 times per day at the amount of 0.001-1000 µg/kg per day, more preferably 0.01-100 µg/kg, most preferably 0.1-10 µg/kg.

A typical treatment regimen entails administering to a human patient a composition containing from about 10 to about 100 µg of active ingredient according to the invention from one to three times daily, with about 15-50 µg two times per day being preferred. The composition for the oral administration may be administered with or without food and/or water.

The composition of the present invention may further contain physiologically acceptable additives. Said additives may include the ingredients used with the present compounds such as excipient, diluent, filler, resolvent, lubricant, adjuvant, binder, disintegrator, emulsifier, dispersing agent, suspending agent, thickener, tonicity agent, buffering agent, soothing agent, preservative, antioxidant, corrigent, flavor, colorant, a functional material such as cyclodextrin and biodegradable polymer, stabilizer. They may be further dissolved in an appropriate solvent such as fatty acid or its mono, di or triglyceride. The additives are well known to the art and may be selected from those described in general reference books of pharmaceutics.

The amount of the above-defined compound in the composition of the invention may vary depending on the formulation of the composition, and may generally be 0.00001-10.0 wt %, more preferably 0.0001-1.0 wt %, most preferably 0.001-0.1%.

The term "treatment" used herein includes any means of control such as prevention, care, relief of the condition, attenuation of the condition and arrest of progression.

The composition of the present invention may further contain other pharmacological ingredients as far as they do not contradict the purpose of the present invention.

The present invention can provide an enteric coated composition for oral administration of a chloride channel opener which can provide improved pharmaceutical effect to the living body. Further, the enteric coated composition such as tablet, capsule, powder and granule may be beneficial to prevent irritation of the upper gastric organs, such as nausea, vomiting, acid reflux and so forth subsequently reduce adverse events due to the irritation by the chloride channel opener, especially prostaglandin compound.

The present invention will be further illustrated with reference to test examples, which, however, are not intended to limit the present invention.

TEST EXAMPLE 1

The difference of nausea observation after the oral administration was investigated between the enteric coated formulation containing 13,14-dihydro-15-keto-16,16-difluoro-$PGE_1$ (compound 1) and the formulation without enteric coating.

The result suggests that the enteric coated formulation results in reduced nausea compared with a formulation without enteric coating.

TEST EXAMPLE 2

The ratio of monocyclic/bicyclic of compound 1 shown below may vary depending on the condition. When provided as a solid compound, substantially 100% of the compound 1 exists as the bicyclic structure.

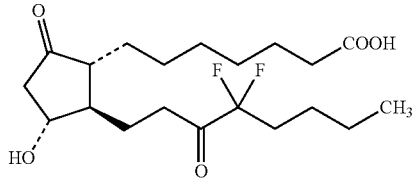

Monocyclic

According to the same manner described in the test example 2, the ratio of monocyclic tautomer/bicyclic tautomer of compound 2 in pH2 solvent was determined by $^1$H-NMR. The result is shown in Table 2 below.

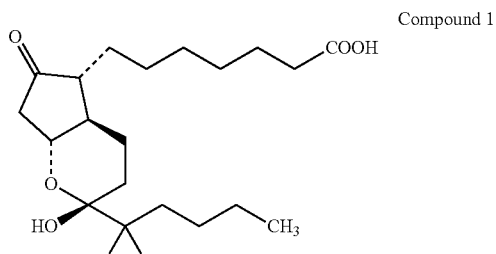

Compound 1 bicyclic

The compound 1 (bicyclic structure, solid) was dissolved in $D_2O$—$CD_3OD$(1:1), which was adjusted to pH 2 with DCl. The ratio of monocyclic tautomer/bicyclic tautomer of compound 1 in the pH2 solvent was determined with $^1$H-NMR. The result is shown in Table 1 below.

TABLE 1

| | Ratio of Monocyclic tautomer of compound 1 in pH2 solvent |
|---|---|
| Solvent | Ratio of monocyclic tautomer (%) Compound 1 |
| $D_2O$-$CD_3OD$ (1:1) pH2 | 8.5 |

The data suggests that the bicyclic ring of the bicyclic tautomer of compound 1 was opened in the pH2 solvent and more than 5% of the compound converted into the monocyclic tautomer.

TEST EXAMPLE 3

A solid preparation of compound 2 which consists of substantially 100% bicyclic tautomer was used.

TABLE 2

| | Ratio of Monocyclic tautomer of compound 2 in pH2 solvent |
|---|---|
| | Table 2 |
| Solvent | Ratio of monocyclic tautomer (%) Compound 2 |
| $D_2O$-$CD_3OD$ (1:1) pH2 | 8.5 |

The data suggests that the bicyclic ring of the bicyclic tautomer of compound 2 was opened in the pH2 solvent and more than 5% of the compound converted into the monocyclic tautomer.

FORMULATION EXAMPLE

Enteric coated capsule was obtained by spraying hydroxypropyl methylcellulose phthalate as enteric coating equally to the gelatin soft capsule in which includes 13,14-dihydro-15-keto-16,16-difluoro-PGE$_1$.

The invention claimed is:
1. A composition for oral administration, comprising a bicyclic compound of

Compound 2

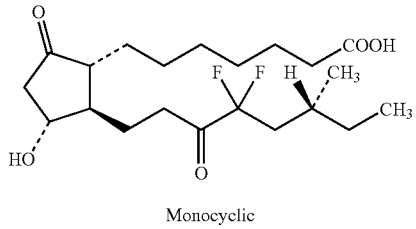

Monocyclic

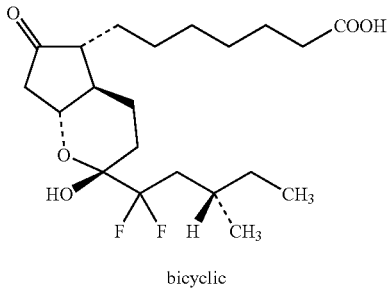

bicyclic

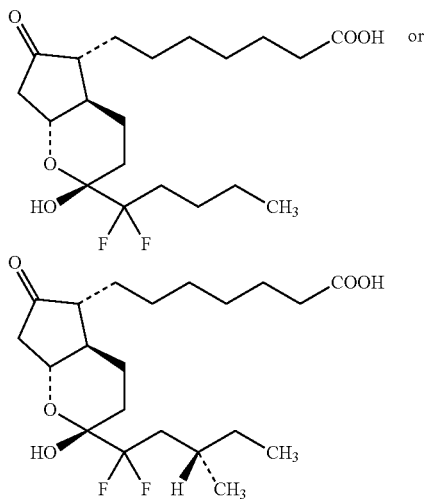
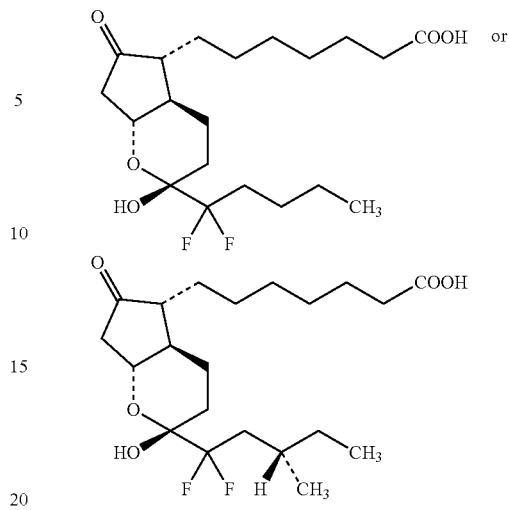

as an active ingredient thereof and an enteric coating, wherein the bicyclic compound is present in the composition together with its monocyclic tautomer in a bicyclic:monocyclic ratio of at least 20:1.

2. The composition as described in claim 1, wherein said composition exhibits reduced nausea inducing effect than that of a composition without the enteric coating.

3. The composition as described in claim 1, wherein said enteric coating is selected from the group consisting of carboxymethyl ethylcellulose, hydroxypropyl methylcellulose phthalate, cellulose acetate phthalate, cellulose acetate butylate, cellulose acetate trimellitate, hydroxypropyl methylcellulose acetate succinate, and a methacrylic acid copolymer.

4. The composition as described in claim 1, wherein said composition is for preventing irritation of upper gastric organs.

5. The composition as described in claim 1, wherein said composition is for improving pharmacological effect of the bicyclic compound to a living body.

6. The composition as described in claim 1; wherein the composition further comprises a solvent comprising a fatty acid or its mono, di or triglyceride.

7. A composition for oral administration, comprising a bicyclic compound of as an active ingredient thereof and an enteric coating, wherein the bicyclic compound is present in the composition together with its monocyclic tautomer in a bicyclic:monocyclic ratio of at least 20:1, and
wherein the composition further comprises a solvent comprising a fatty acid or its mono, di or triglyceride.

8. The composition as described in claim 7, wherein said composition exhibits reduced nausea inducing effect than that of a composition without the enteric coating.

9. The composition as described in claim 7, wherein said enteric coating is selected from the group consisting of carboxymethyl ethylcellulose, hydroxypropyl methylcellulose phthalate, cellulose acetate phthalate, cellulose acetate butylate, cellulose acetate trimellitate, hydroxypropyl methylcellulose acetate succinate, and a methacrylic acid copolymer.

10. The composition as described in claim 7, wherein said composition is for preventing irritation of upper gastric organs.

11. The composition as described in claim 7, wherein said composition is for improving pharmacological effect of the bicyclic compound to a living body.

\* \* \* \* \*